United States Patent
Yokotagawa et al.

(10) Patent No.: US 7,396,816 B2
(45) Date of Patent: Jul. 8, 2008

(54) LOW-MOLECULAR WEIGHT PEPTIDES INHIBITING ION CHANNEL ACTIVITY

(75) Inventors: Takane Yokotagawa, Tokyo (JP); Masahiro Sokabe, Aichi (JP); Toshio Furuya, Tokyo (JP)

(73) Assignee: Pharmadesign, Inc., Tokyo (JP)

( * ) Notice: Subject to any disclaimer, the term of this patent is extended or adjusted under 35 U.S.C. 154(b) by 76 days.

(21) Appl. No.: 10/550,102

(22) PCT Filed: Mar. 25, 2004

(86) PCT No.: PCT/JP2004/004190

§ 371 (c)(1),
(2), (4) Date: Sep. 21, 2005

(87) PCT Pub. No.: WO2004/085647

PCT Pub. Date: Oct. 7, 2004

(65) Prior Publication Data

US 2006/0229434 A1 Oct. 12, 2006

(30) Foreign Application Priority Data

Mar. 26, 2003 (JP) .............................. 2003-085666

(51) Int. Cl.
*A61K 38/08* (2006.01)
*A61K 38/04* (2006.01)

(52) U.S. Cl. ............................................ 514/15; 514/2

(58) Field of Classification Search ........................ None
See application file for complete search history.

(56) References Cited

FOREIGN PATENT DOCUMENTS

WO    WO 01/76618    10/2001

OTHER PUBLICATIONS

Bowie Ju et al., Deciphering the message in protein sequences:tolerance to amino acid substitutions, Mar. 1990, Science, v247 pp. 1306-1310.*

Robert E. Oswald et al., "Solution Structure of Peptide Toxins That Block Mechanosensitive Ion Channels", Journal of Biological Chemistry, Sep. 13, 2002, pp. 34443-34450, vol. 27, No. 37, American Society of Biological Chemical Biologists, Birmingham, U.S.A.

Kimberly Laskie Ostrow et al., "cDNA sequence and in vitro folding of GsMT=4, a specific peptide inhibitor of mechanosensitive channels", TOXICON, vol. 42, No. 3, Sep. 3, 2003, pp. 263-274.

Philip A. Gottlieb et al., "Mechanosensitive Ion Channels as Drug Targets",Current Drug Targets. CNS & Neurological Disorders, 2004, pp. 287-295, vol. 3, No. 4, Bentham Science Publishers, Hilversum, Netherlands.

European Search Report dated Apr. 19, 2006, issued in correspondong European Patent Application No. EP 04723309.3.

T. M. Suchyna et al.; "Identification of a Peptide Toxin from *Grammostola spatulata* Spider Venom that Blocks Cation-selective Stretch-activated Channels", The Journal of General Physiology, vol. 115, No. 5, 2000, pp. 583-598. Cited in ISR.

Frank Bode et al.; "Tarantula peptide inhibits atrial fibrillation", Nature, vol. 409, No. 6816, 2001, pp. 35-36. Cited in ISR.

Owen White et al.; "Genome Sequence of the Radioresistant Bacterium Deinococcus radiodurans R1", Science, vol. 286, 1999, pp. 1571-1577. Cited in ISR.

S. R. H. Russell et al.; "*Dropophila melanogaster* Male Germ Line-Specific Transcripts With Autosomal and Y-Linked Genes", Genetics, vol. 134, 1993, pp. 293-308. Cited in ISR.

* cited by examiner

*Primary Examiner*—Anish Gupta
*Assistant Examiner*—Ronald T Niebauer
(74) *Attorney, Agent, or Firm*—Westerman, Hattori, Daniels & Adrian, LLP.

(57) ABSTRACT

It is intended to provide novel polypeptides which specifically inhibit the activity of a mechano-sensitive channel; and mechano-sensitive channel inhibitors or remedies for atrial fibrillation containing these polypeptides or salts thereof. The above objects can be achieved by using polypeptides having amino acid sequences represented by SEQ ID NO:1 (TVP003), SEQ ID NO:2 (TVP004) and SEQ ID NO:3 (TVP005), salts of these polypeptides, and mechano-sensitive channel inhibitors or remedies for atrial fibrillation containing the same.

2 Claims, 11 Drawing Sheets

Fig. 1

| | | |
|---|---|---|
| 1QDP__ | ----CAKKRNWCG----KNEDCCCP-MKCIYAWYNQQGSCQTTITGLFKKC | SEQ ID |
| 1VTX__ | ----CAKKRNWCG----KTEDCCCP-MKCVYAWYNEQGSCQSTISALWKKC | SEQ ID |
| 1EMX_A | -DDCGKLFSGCD----TNADCCEG-YVCR--------LWCK---LD--W-- | SEQ ID |
| 1QK7_A | ---GC--LGDKCD----YNNGCCSG-YVCSRTW-----KWCV--LAGPW-- | SEQ ID |
| 1EIU__ | ---ACVGENQQCADW-AGPHCCDG-YYCTCRYF----PKCICRNNN----- | SEQ ID |
| 1EIV__ | ---ACVGENQQCADW-AGPHCCDG-YYCTCRYF----PKCICRNNN----- | SEQ ID NO: |
| 1EIT__ | ---ECVPENGHCRDW-YD-ECCEG-FYCSCRQP----PKCICRNNNX---- | SEQ ID NO: |
| 1QK6_A | ---ACKGVFDACTP--GKNECCPN-RVCSDKH------KWCKWKL------ | SEQ ID NO: |
| GSMTX4 | ---GCLEFWWKCNP--NDDKCCRPKLKCSKLF------KLCNPSSG----- | SEQ ID NO: |
| 1I25_A | LFECS----PSCEIEKEGDKPCKK-KKCKGGW------KCKFNMCVKV--- | SEQ ID NO: |

Fig. 2

The alignment of 1OK6 and

| | | |
|---|---|---|
| 1QK6 | ACKGVFDACTPGKNECC-PNRVCSDKHKWCKWKL- | SEQ ID NO: |
| GSMTX4 | GCLEFWWKCNPNDDKCCRPKLKCSKLFKLCNPSSG | SEQ ID |
| | .*  .:  *.*,.::** *:  **. .* *::. | % identity: 30.3 |

( Alignment : Clustalw 1.81)

Fig.9
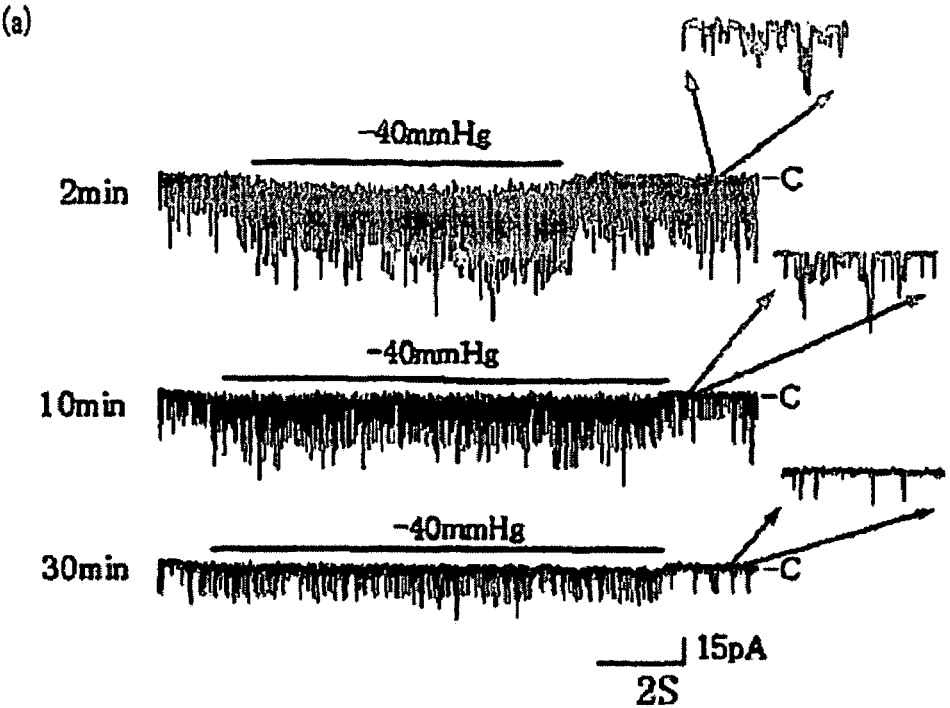
(a)
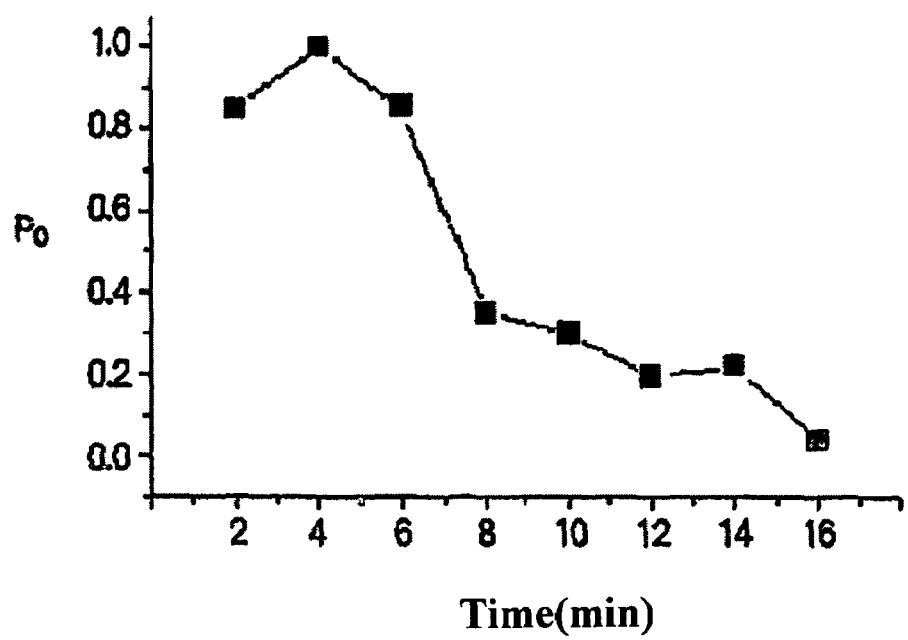
(b)

Fig.10
(a)
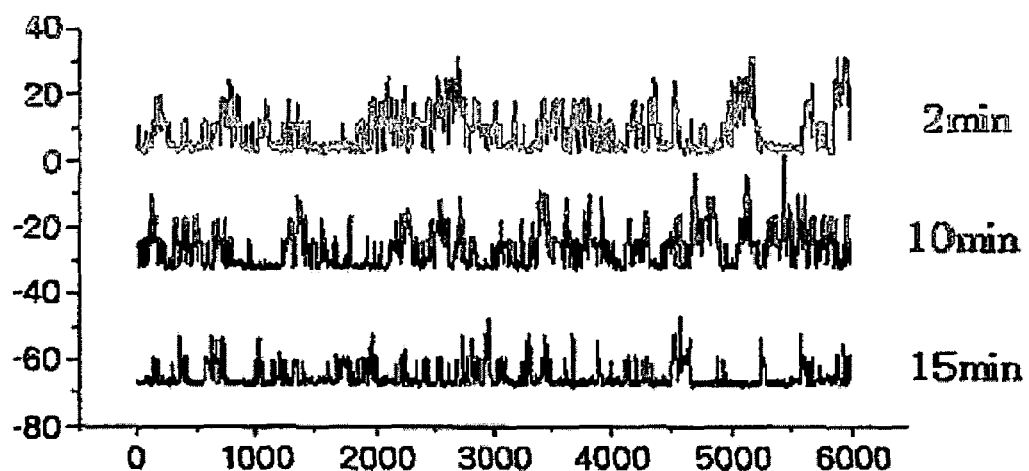
(b)
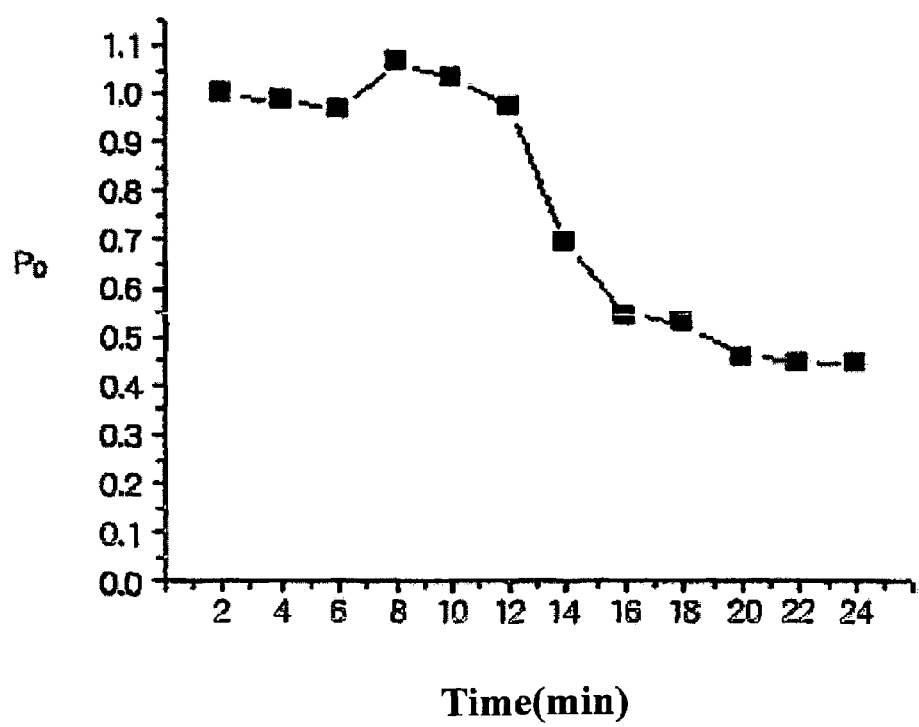
Time(min)

Fig.11
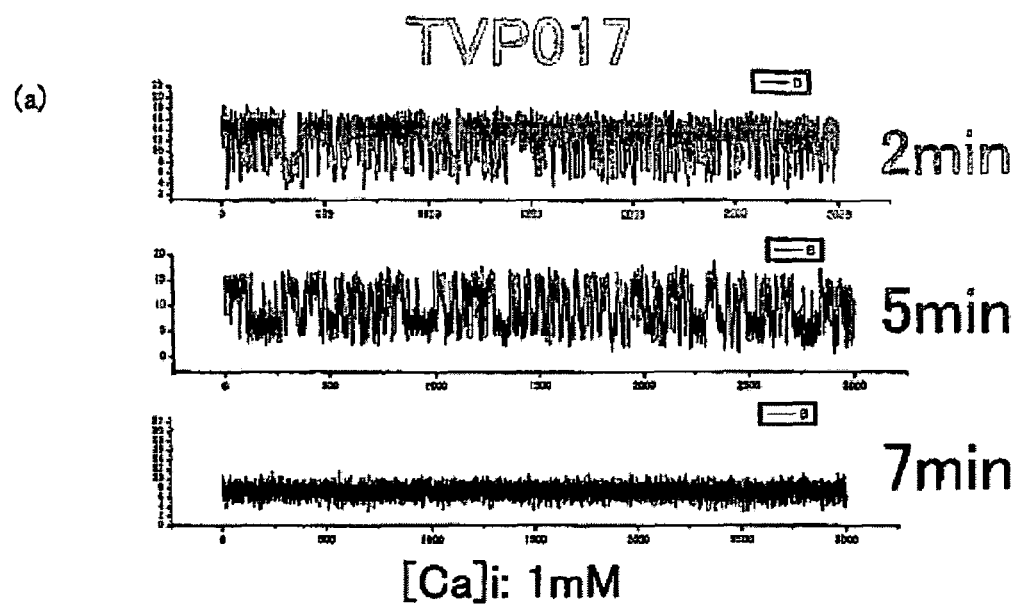
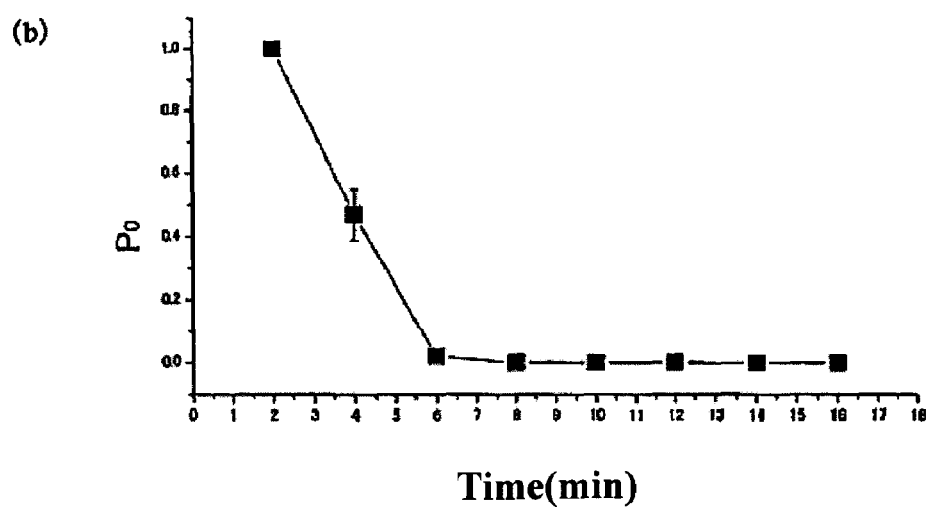

SEQUENCE LISTING

```
<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:Synthetic
      Polypeptide

<400> SEQUENCE: 1

Trp Lys Cys Asn Pro Asn Asp Asp Lys Cys
1               5                   10

<210> SEQ ID NO 2
<211> LENGTH: 8
```

```
<212> TYPE: PRT
<213> ORGANISM: Artificial Sequence
<220> FEATURE:
<223> OTHER INFORMATION: Description of Artificial Sequence:Synthetic
      Polypeptide

<400> SEQUENCE: 2

Cys Ala Arg Pro Lys Leu Lys Cys
 1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence:Synthetic
      Polypeptide

<400> SEQUENCE: 3

Trp Lys Cys Asn Pro Asn Asp Asp Lys Ala Ala Arg Pro Lys Leu Lys
 1               5                  10                  15

Cys

<210> SEQ ID NO 4
<211> LENGTH: 35
<212> TYPE: PRT
<213> ORGANISM: Grammostola spatulata

<400> SEQUENCE: 4

Gly Cys Leu Glu Phe Trp Trp Lys Cys Asn Pro Asn Asp Asp Lys Cys
 1               5                  10                  15

Cys Arg Pro Lys Leu Lys Cys Ser Lys Leu Phe Lys Leu Cys Asn Phe
                20                  25                  30

Ser Ser Gly
        35

<210> SEQ ID NO 5
<211> LENGTH: 42
<212> TYPE: PRT
<213> ORGANISM: Atrax robustus

<400> SEQUENCE: 5

Cys Ala Lys Lys Arg Asn Trp Cys Gly Lys Asn Glu Asp Cys Cys Cys
 1               5                  10                  15

Pro Met Lys Cys Ile Tyr Ala Trp Tyr Asn Gln Gln Gly Ser Cys Gln
                20                  25                  30

Thr Thr Ile Thr Gly Leu Phe Lys Lys Cys
        35                  40

<210> SEQ ID NO 6
<211> LENGTH: 42
<212> TYPE: PRT
<213> ORGANISM: Hadronyche versuta

<400> SEQUENCE: 6

Cys Ala Lys Lys Arg Asn Trp Cys Gly Lys Thr Glu Asp Cys Cys Cys
 1               5                  10                  15

Pro Met Lys Cys Val Tyr Ala Trp Tyr Asn Glu Gln Gly Ser Cys Gln
                20                  25                  30

Ser Thr Ile Ser Ala Leu Trp Lys Lys Cys
        35                  40
```

```
<210> SEQ ID NO 7
<211> LENGTH: 30
<212> TYPE: PRT
<213> ORGANISM: Heteropodidae veratoria

<400> SEQUENCE: 7

Asp Asp Cys Gly Lys Leu Phe Ser Gly Cys Asp Thr Asn Ala Asp Cys
1               5                   10                  15

Cys Glu Gly Tyr Val Cys Arg Leu Trp Cys Lys Leu Asp Trp
            20                  25                  30

<210> SEQ ID NO 8
<211> LENGTH: 32
<212> TYPE: PRT
<213> ORGANISM: Selenocosmia huwena

<400> SEQUENCE: 8

Gly Cys Leu Gly Asp Lys Cys Asp Tyr Asn Asn Gly Cys Cys Ser Gly
1               5                   10                  15

Tyr Val Cys Ser Arg Thr Trp Lys Trp Cys Val Leu Ala Gly Pro Trp
            20                  25                  30

<210> SEQ ID NO 9
<211> LENGTH: 37
<212> TYPE: PRT
<213> ORGANISM: Agelenopsis aperta

<400> SEQUENCE: 9

Ala Cys Val Gly Glu Asn Gln Gln Cys Ala Asp Trp Ala Gly Pro His
1               5                   10                  15

Cys Cys Asp Gly Tyr Tyr Cys Thr Cys Arg Tyr Phe Pro Lys Cys Ile
            20                  25                  30

Cys Arg Asn Asn Asn
            35

<210> SEQ ID NO 10
<211> LENGTH: 37
<212> TYPE: PRT
<213> ORGANISM: Agelenopsis aperta

<400> SEQUENCE: 10

Ala Cys Val Gly Glu Asn Gln Gln Cys Ala Asp Trp Ala Gly Pro His
1               5                   10                  15

Cys Cys Asp Gly Tyr Tyr Cys Thr Cys Arg Tyr Phe Pro Lys Cys Ile
            20                  25                  30

Cys Arg Asn Asn Asn
            35

<210> SEQ ID NO 11
<211> LENGTH: 37
<212> TYPE: PRT
<213> ORGANISM: Agelenopsis aperta
<220> FEATURE:
<221> NAME/KEY: UNSURE
<222> LOCATION: (37)
<223> OTHER INFORMATION: Xaa represents unknown amino acid residue

<400> SEQUENCE: 11

Glu Cys Val Pro Glu Asn Gly His Cys Arg Asp Trp Tyr Asp Glu Cys
1               5                   10                  15

Cys Glu Gly Phe Tyr Cys Ser Cys Arg Gln Pro Pro Lys Cys Ile Cys
            20                  25                  30
```

```
Arg Asn Asn Asn Xaa
            35

<210> SEQ ID NO 12
<211> LENGTH: 33
<212> TYPE: PRT
<213> ORGANISM: Selenocosmia huwena

<400> SEQUENCE: 12

Ala Cys Lys Gly Val Phe Asp Ala Cys Thr Pro Gly Lys Asn Glu Cys
 1               5                  10                  15

Cys Pro Asn Arg Val Cys Ser Asp Lys His Lys Trp Cys Lys Trp Lys
                20                  25                  30

Leu

<210> SEQ ID NO 13
<211> LENGTH: 37
<212> TYPE: PRT
<213> ORGANISM: Selenocosmia huwena

<400> SEQUENCE: 13

Leu Phe Glu Cys Ser Phe Ser Cys Glu Ile Glu Lys Glu Gly Asp Lys
 1               5                  10                  15

Pro Cys Lys Lys Lys Lys Cys Lys Gly Gly Trp Lys Cys Lys Phe Asn
                20                  25                  30

Met Cys Val Lys Val
            35

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence:Synthetic
      Polypeptide

<400> SEQUENCE: 14

Gly Cys Leu Glu Phe Trp Trp Lys Ala Asn Pro Asn Asp Asp Lys Ala
 1               5                  10                  15

Cys

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence:Synthetic
      Polypeptide

<400> SEQUENCE: 15

Cys Ala Arg Pro Lys Leu Lys Ala Ser Lys Leu Phe Lys Leu Cys
 1               5                  10                  15

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:Synthetic
      Polypeptide

<400> SEQUENCE: 16

Cys Ala Ala Pro Lys Leu Lys Cys
 1               5
```

```
<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:Synthetic
      Polypeptide

<400> SEQUENCE: 17

Cys Ala Arg Pro Lys Leu Ala Cys
  1               5
```

LOW-MOLECULAR WEIGHT PEPTIDES INHIBITING ION CHANNEL ACTIVITY

DETAILED DESCRIPTION OF THE INVENTION

1. Field of the Invention

The present invention relates to a polypeptide that inhibits the activity of a mechano-sensitive channel, and relates to a mechano-sensitive channel inhibitor and remedy for atrial fibrillation comprising the polypeptide. More specifically, the present invention determines the pharmacophore that acts upon the mechano-sensitive channel based on the sequence of a natural peptide from spider venom (GsMTx-4), and it relates to novel polypeptides designed to compose the pharmacophore which are moreover useful for atrial fibrillation treatment.

2. Background of Art

Atrial fibrillation is a type of arrhythmia, of which the morbidity prevalence rate increases with advanced age. Atrial fibrillation is a heart disease observed in 3% of the elderly (over 65 years old). When atrial fibrillation becomes chronic, it forms a thrombosis and induces cerebral thrombosis, and therefore it is currently thought that atrial fibrillation is the main disease factor of serious cases of cerebral apoplexy. Thus, considering the frequency and seriousness of complications such as cerebral infarction, atrial fibrillation has come to be regarded in recent years as one kind of lethal arrhythmia (J. Nippon. Med. Sch. 2002, 69(3)). Heretofore, a remedy that completely cures atrial fibrillation had not been obtained, and so it had been assumed that medication for atrial fibrillation, particularly chronic atrial fibrillation, had its limits (J. Nippon. Med. Sch. 2002, 69(3)).

Atrial fibrillation is believed to be caused in part by the malfunctioning of an ion channel in the myocardium. Meanwhile, a natural peptide from spider venom (GsMTx-4: SEQ ID NO:4) is known to inhibit the activity of a mechano-sensitive channel (Stretch-Activated Channel: SAC) (see for example Thomas M. Suchyna et al., Identification of a Peptide Toxin from Grammostola Spatulata Spider Venom that Blocks Cation-selective Stretch-activated Channels, J. Gen. Physiol., Vol. 115, pp 583-598 (2000) (non-patent document 1)). In the said document, it is described that in peptides composing toxins derived from venoms from terrestrial and aquatic animals, an ICK (Inhibitor Cysteine Knot) motif with six cysteines is commonly observed (non-patent document 1, p. 590, right column, 1 1.7 to 3 from bottom, and FIG. 30). The said document also suggests that GsMTx-4 has an ICK motif with a basic structure defined by three cysteine pairs ($C_1$-$C_4$, $C_2$-$C_5$ and $C_3$-$C_6$) (non-patent document 1, p. 595, left column, 1.7 to 1.11 from bottom, column 'The structure of GsMTx-4').

Furthermore, methods for extracting and purifying GsMTx-4, methods for treating cerebral arrhythmia with the said GsMTx-4 and so forth have been suggested (see for example Bode et al., Nature, Vol. 409, pp 35-36 (2001) (non-patent document 2), U.S. Patent Application Published Description No.2002/0077286 (patent document 1)). Further, the structure of GsMTx-4 has been known from results obtained in a solution using NMR (see Robert et al., J. Biol. Chem. Vol. 37, pp 3443-3445, 2002. (non-patent document 3)). Despite such findings, a remedy for atrial fibrillation using the peptide derived from spider venom (GsMTx-4) had not been developed.

REFERENCES

Patent document 1: U.S. Patent Application Published Description No.2002/0077286;

Non-patent document 1: Thomas M. Suchyna et.al., Identification of a Peptide Toxin from Grammostola Spatulata Spider Venom that Blocks Cation-selective Stretch-activated Channels, J. Gen. Physiol., Vol. 115, pp 583-598 (2000);

Non-patent document 2: Bode et al., Nature, Vol. 409, pp 35-36 (2001);

Non-patent document 3: Robert et al., J. Biol. Chem. Vol. 37, pp 3443-3445 (2002).

The object of the present invention is to identify the pharmacophore (the minimum space structure needed for activation) of GsMTx-4, to design novel polypeptides that specifically inhibit the activity of a mechano-sensitive channel based on the pharmacophore information, and to provide remedies for atrial fibrillation comprising such polypeptides.

SUMMARY OF INVENTION

The above objects are achieved by the following inventions.

[1] In a first aspect of the present invention, it involves a polypeptide or salts thereof consisting of an amino acid sequence represented by SEQ ID NO:1, SEQ ID NO:2 or SEQ ID NO:3. These polypeptides, as confirmed in the embodiment of this description, are polypeptides that show mechano-sensitive channel inhibiting activity, and can be considered as polypeptides that compose the pharmacophore of GsMTx-4. These polypeptides are useful for treatment of atrial fibrillation and such.

[2] In a second aspect of the present invention, it involves a polypeptide or salts thereof comprising an amino acid sequence represented by SEQ ID NO:1, SEQ ID NO:2 or SEQ ID NO:3.

[3] In a third aspect of the present invention, it involves a polypeptide or salts thereof consisting of an amino acid sequence represented by SEQ ID NO:16 or SEQ ID NO:17. These polypeptides, as confirmed in the embodiment of this description, are polypeptides that show mechano-sensitive channel inhibiting activity. These polypeptides are useful for treatment of atrial fibrillation and such.

[4] In a fourth aspect of the present invention, it involves a polypeptide or salts thereof consisting of an amino acid sequence represented by SEQ ID NO:1, SEQ ID NO:2 or SEQ ID NO:3 of which one or more of the amino acids thereof have been deleted, substituted, inserted or added, but not comprising an amino acid sequence described in SEQ ID NO:4, and moreover showing mechano-sensitive channel inhibiting activity.

[5] In a fifth aspect of the present invention, it involves a polypeptide or salts thereof described in the above [4] as consisting of an amino acid sequence represented by SEQ ID NO:1, SEQ ID NO:2 or SEQ ID NO:3 of which one or more of the amino acids thereof have been deleted, substituted, inserted or added, but not comprising an amino acid sequence described in SEQ ID NO:4, and moreover showing mechano-sensitive channel inhibiting activity, of which the said polypeptide comprises an amino acid sequence represented by SEQ ID NO:16 or SEQ ID NO:17.

[6] In a sixth aspect of the present invention, it involves a polynucleotide comprising a polynucleotide that encodes the polypeptide described in the above [1], the above [3] or the above [4].

[7] In a seventh aspect of the present invention, it involves a recombinant vector comprising the polynucleotide described in the above [6].

[8] In an eighth aspect of the present invention, it involves a transformant transformed by the recombinant vector described in the above [7].

[9] In a ninth aspect of the present invention, it involves a mechano-sensitive channel inhibitor comprising one or more of the polypeptides or salts thereof described in one of the above [1] to [5]. This inhibitor specifically inhibits the activity of a mechano-sensitive channel and thus is useful for conducting researches on mechano-sensitive channels and such.

[10] In a tenth aspect of the present invention, it involves a remedy for atrial fibrillation comprising one or more of the polypeptides or salts thereof described in one of the above [1] to [5]. These polypeptides, as confirmed of their functions in the embodiment of this description, show mechano-sensitive channel inhibiting activity. Therefore, this remedy can be used effectively in treating atrial fibrillation.

BRIEF DESCRIPTION OF THE DRAWINGS

FIG. 1 is a representation of the ten prospective multiple alignments showing high homology to GsMTx-4

FIG. 2 is a representation of the alignment of 1QK6 and GsMTx-4.

In FIG. 4, the thin lines indicate the template and the thick lines indicate GsMTx-4.

In FIG. 5, the thin lines indicate Huwentoxin-I and the thick lines indicate GsMTx-4.

In FIGS. 6(a) to 6(d), the left side indicates Huwentoxin-I, and the right side indicates GsMTx-4. FIG. 6(a) is a view of the model from a hydrophobic patch (approximately the same direction as the drawings above). FIG. 6(b) is a view of the model rotated +90° around the x-axis. FIG. 6(c) is a view of the model rotated +90° around the y-axis. FIG. 6(d) is a view of the model rotated 180° around the y-axis.

FIG. 8(a) is a representation of the single channel current recordings. FIG. 8(b) represents the channel's open probability (Po).

FIGS. 9(a) and 9(b) are representations of the inhibiting activity of TVP004. FIG. 9(a) is a representation of the single channel current recordings. FIG. 9(b) represents the channel's open probability (Po).

FIGS. 10(a) and 10(b) are representations of the inhibiting activity of TVP005. FIG. 10(a) is a representation of the single channel current recordings. FIG. 10(b) represents the channel's open probability (Po).

FIGS. 11(a) and 11(b) are representations of the inhibiting activity of TVP017. FIG. 11(a) is a representation of the single channel current recordings. FIG. 11(b) represents the channel's open probability (Po).

FIG. 12(a) is a representation of the single channel current recordings. FIG. 12(b) represents the channel's open probability (Po).

FIG. 13(a) is a representation of the single channel current recordings related to the myocardial SA channel of TVP003. FIG. 13(b) is a representation of the single channel current recordings related to the STREX-deletion-mutant of TVP0003. FIG. 13(c) represents the channel's open probability (Po).

BEST MODE FOR CARRYING OUT THE INVENTION

Polypeptides of the Present Invention

Figure 3:
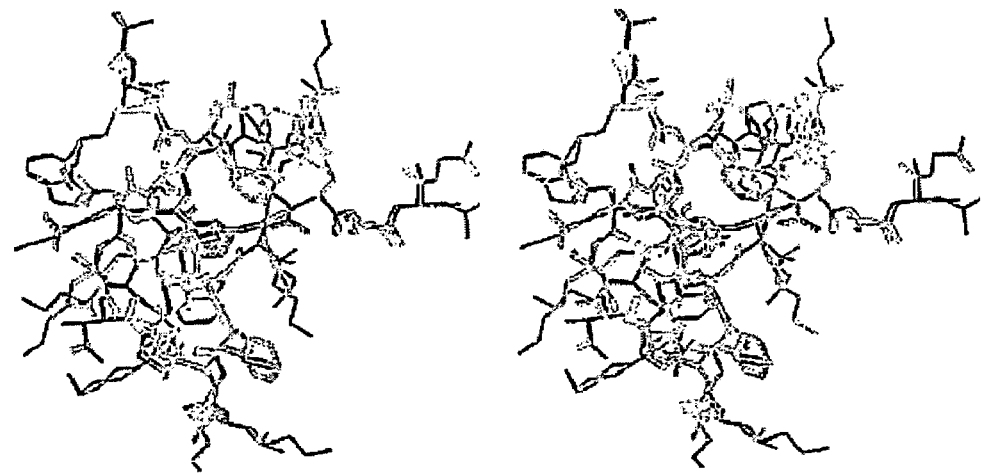
FIG. 3 is a stereo view superimposing Huwentoxin-I and GsMTx-4.

The Polypeptides of the present invention consist of a polypeptide consisting of an amino acid sequence represented by SEQ ID NO:1, SEQ ID NO:2 or SEQ ID NO:3; a polypeptide comprising an amino acid sequence represented by SEQ ID NO:1, SEQ ID NO:2 or SEQ ID NO:3; a polypeptide consisting of an amino acid sequence represented by SEQ ID NO:16 or SEQ ID NO:17; a polypeptide consisting of an amino acid sequence represented by SEQ ID NO:1, SEQ ID NO:2 or SEQ ID NO:3 of which one or more of the amino acids have been deleted, substituted, inserted or added, but not comprising an amino acid sequence described in SEQ ID NO:4, and moreover showing mechano-sensitive channel inhibiting activity (namely, the polypeptides involved in embodiments 1 to 5 of the present invention).

Furthermore, the polypeptides of the present invention may have a C-terminus in the form of a carboxyl group (—COOH), a carboxylate (—COO⁻), an amide (—CONH$_2$), an ester (—COOR) or the like.

The polypeptides of the present invention include polypeptides wherein the amino group at the methionine residue of the N-terminus is protected with a protecting group. The polypeptides of the present invention include polypeptides wherein the N-terminal is cleaved in vivo and the Gln thus formed is pyroglutaminated. The polypeptides of the present invention include polypeptides wherein a substituent on a side chain is protected by an appropriate protecting group. The polypeptides of the present invention include synthetic polypeptides such as the so-called glycoproteins having conjugated sugar chains.

The salts of the polypeptides of the present invention may be salts in the form of physiologically acceptable salts with acids or bases, preferably in the form of physiologically acceptable acid addition salts. Examples of such salts include salts with inorganic acids (e.g. hydrochloric acid, phosphoric acid, hydrobromic acid, sulfric acid), and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzensulfonic acid).

Composition of the Polypeptides of the Present Invention

The polypeptides of the present invention may be prepared by chemical synthesis, or may be manufactured using recombinant DNA technology. To prepare the polypeptides of the present invention by chemical synthesis, the publicly known methods may be used, for example, the peptide of the present invention can be obtained by methods using azide, acid chloride, acid anhydride, compound acid anhydride, DCC, activated ester, Woodward's reagent K, carbonylimidazole, deoxidization, DCC/HONB, BOP reagent (see for example Bozanszky, M and M. A. Ondetti, Peptide Synthesis, Interscience Publishers, New York (1966); Schroeder and Luebke, The Peptide, Academic Press, New York (1965); F. M. Finn and K. Hofinann, The Proteins Vol. 2, H. Nenrath, R. L. Hill ed., Academic Press Inc., New York (1976); Nobuo Izumiya et al., *Peptide Gosei no Kiso to Jikken* (Basics and experiments of peptide synthesis), Maruzen Co. (1985); Haruaki Yajima and Shunpei Sakakibara et al., *Seikagaku Jikken Koza* (Biochemical Experiment) 1, Japanese Biochemical Society ed., Tokyo Kagaku Dojin Co. (1977); Toshiya Kimura, *Zoku Seikagaku Jikken Koza* (Sequel to Biochemical Experiment) 2, Japanese Biochemical Society ed., Tokyo Kagaku Dojin Co. (1987)). Furthermore, the peptide of the present invention can be prepared by chemical synthesis using an automated peptide synthesizer (e.g. PE Applied Bio Systems Co.).

Further, following the completion of reaction, the polypeptides of the present invention can be purified and separated by publicly known purification methods. For example, the polypeptide of the present invention can be purified and separated by a combination of solvent extraction, distillation, column chromatography, liquid chromatography, recrystallization and the like. Where the peptide of the present invention obtained by the above methods is in a free form, publicly known methods can be used to convert it into a salt form, and on the other hand, where the peptide is obtained in a salt form, publicly known methods can be used to convert it into a free form.

Polynucleotide Encoding the Polypeptide

The polynucleotide encoding the polypeptide of the present invention may be any polynucleotide so long as it contains the base sequence (DNA or RNA, preferably DNA) encoding the polypeptide of the present invention. For example, the polynucleotide may be the DNA or RNA such as MRNA encoding the polypeptide of the present invention, and it can either be double stranded or single stranded. When double stranded, it may be a double stranded DNA, a double stranded RNA or a hybrid of DNA and RNA. When single stranded, it may either be a sense strand (namely, a coding strand) or an anti-sense strand (namely, a non-coding strand).

Using the polynucleotide encoding the polypeptide of the present invention, mRNA of the polypeptide of the present invention can be assayed, for example, according to the publicly known method described in the special issue of *Jikken Igaku* (Experimental Medicine), *Shin PCR to Sono Oyo* (Novel PCR and its application) 15(7), 1997, or according to a similar method.

The DNA encoding the polypeptide of the present invention include genomic DNA, genomic DNA library, cDNA derived from the cells or tissues described above, cDNA library derived from the cells and tissues described above, and synthetic DNA, of which any one thereof can be employed. Examples of the vector used for the library include bacteriophage, plasmid, cosmid and phagemide, of which any one thereof can be employed. Further, the DNA can be directly amplified by Reverse Transcriptase Polymerase Chain Reaction (hereinafter abbreviated as RT-PCR) employing a total RNA or a MRNA fraction prepared from the cells or tissues described above.

For cloning the DNA encoding the polypeptide of the present invention, there is the method of amplifying by PCR using synthetic DNA primers comprising a part of the base sequence of the DNA encoding the polypeptide of the present invention. The cloning of the DNA encoding the polypeptide of the present invention can also be performed by selecting the DNA inserted into an appropriate vector by hybridization with a labeled DNA fragment or synthetic DNA that encodes a part of the region or the entire region of the polypeptide of the present invention. Hybridization can be carried out, for example, according to the method described in Molecular Cloning 2nd (J. Sambrook et al., Cold Spring Harbor Lab. Press, 1989). When using commercially available library, hybridization can be carried out according to the method described in the attached instructions.

Substitution of the base sequence of the DNA can be carried out by PCR or by using publicly known kits, for example, Mutan™-super Express Km (Takara Shuzo Co.) and Mutan™-K (Takara Shuzo Co.) according to publicly known methods such as ODA-LA PCR, Gapped duplex method and Kunkel method, or according to similar methods.

The cloned DNA encoding the polypeptides can be used as it is, or if desired, used after digesting with a restriction enzyme or after adding a linker thereto. Such DNA can contain ATG as translation initiation codon at the 5' end thereof and can contain TAA, TGA or TAG as translation termination codon at the 3' end thereof. These translation initiation codon and translation termination codon can be added by using an appropriate synthetic DNA adapter.

The expression vector of the polypeptide of the present invention can be manufactured, for example, by excising a desired DNA fragment from the DNA encoding the polypeptide of the present invention and then litigating the DNA fragment downstream of a promoter in an appropriate expression vector.

Examples of the vector include plasmids derived from a *Escherichia coli* (e.g., pCR4, pCR2.1, pBR322, pBR325, pUC12, pUC13), plasmids derived from *Bacillus subtlis* (e.g., pUB110, pTP5, pC194), plasmids derived from yeast (e.g., pSH19, pSH15), bacteriophages such as λ phage, animal viruses such as retrovirus, vaccinia virus and baculovirus, as well as pA1-11, pXT1, pRc/CMV, pRc/RSV and pcDNAI/Neo.

The promoter employed in the present invention can be any promoter so long as it is an appropriate promoter matching the host used for gene expression. For example, when using animal cells as the host, SRα promoter, SV40 promoter, LTR promoter, CMV promoter, HSV-TK promoter or such can be utilized.

Of these, it is preferable to use CMV promoter, SRα promoter or the like. When using bacteria of the genus *Escherichia* as the host, the preferred promoter is trp promoter, 1 ac promoter, recA promoter, λ $P_L$ promoter, 1 pp promoter or the like, when using bacteria of the genus *Bacillus* as the host, the preferred promoter is SPO1 promoter, SPO2 promoter, penP promoter or the like, when using yeast as the host, the preferred promoter is PHO5 promoter, PGK promoter, GAP promoter, ADH promoter or the like. When using insect cells as the host, it is preferable to use polyhedron promoter, P10 promoter or the like.

For the expression vector, in addition to the above examples, those comprising an enhancer, a splicing signal, a poly A addition signal, a selection marker, an SV40 replication origin (hereafter may be abbreviated as SV40ori) or such can be used if so desired. Examples of the selection marker include dihydrofolate reductase (hereinafter may be abbreviated as dhfr) gene (methotrexate (MTX) resistance), amplicillon resistant gene (hereinafter may be abbreviated as $Amp^r$), neomycin resistant gene (hereinafter may be abbreviated as $Neo^r$, G418 resistance) and the like. In particular, when using dhfr gene as the selection marker by employing CHO ($dhfr^-$) cells, the desired gene may be selected using a medium not comprising thymidine.

When necessary, a signal sequence matching the host is added to the N-terminus of the polypeptide of the present invention. When using bacteria of the genus Escherichia as the host, PhoA signal sequence, OmpA signal sequence or such can be utilized, when using bacteria of the genus *Bacillus* as the host, α-amylase signal sequence, subtilisin signal sequence or such can be utilized, when using yeast as the host, MFα signal sequence, SUC2 signal sequence or such can be utilized, and when using animal cells as the host, insulin signal sequence, α-interferon signal sequence, antibody molecule signal sequence or such can be utilized.

Using the vector comprising the DNA encoding the polypeptide of the present invention thus composed, transformants can be manufactured.

Examples of the host include bacteria of the genus *Escherichia*, bacteria of the genus *Bacillus*, yeast, insect cells, insect and animal cells.

Specific examples of the bacteria of the genus *Escherichia* include *Escherichia coli* K12·DH1 (Proc. Natl. Acad. Sci. USA, 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), DH5α (Inoue, H., Nojima, H. and Okayama, H., Gene, 96, 23-28 (1990)), and DHL10B (Proc. Natl. Acad. Sci. USA, 87,4645-4649 (1990)).

Examples of the bacteria of the genus *Bacillus* include *Bacillus subtilis* MI114 (Gene, 24, 255 (1983)), and 207-21 (Journal of Biochemistry, 95, 87 (1984)).

Examples of yeast include *Saccharomyces cerevisiae* AH22, AH22R-, NA87-11A, DKD-5D, 20B-12, *Schizosaccharomyces pombe* NCYC1913,NCYC2036, and *Pichia pastoris*.

For insect cells, where the virus is AcNPV, *Spodoptera frugiperda* cells (Sf cells), MG1 cells derived from the mid-intestine of *Trichoplusia ni*, HighFive™ cells derived from the egg of *Trichoplusoa ni*, cells derived from *Mamestra brassicae*, cells derived from *Estigmena acrea* and the like can be used. Where the virus is BmNPV, *Bombyx mori* N cells (BmN cells) and the like can be used. Examples of the Sf cells thereof include Sf9 cells (ATCC CRL1711), and Sf21 cells (see Vaughn, J. L. et al., In Vivo, 13, 213-217 (1977) for above).

For insects, the larva of silkworms can be used (Maeda et al., Nature, 315, 592 (1985)).

Examples of animal cells include monkey cells COS-7, Vero, Chinese hamster cells CHO (hereinafter abbreviated as CHO cells), dhfr gene deficient Chinese hamster cells CHO (hereinafter abbreviated as CHO(dhfr⁻) cells), mouse L cells, mouse AtT-20, mouse myeloma cells, rat GH3, and human FL cells.

Bacteria of the genus *Escherichia* can be transformed according to the method described, for example, in Proc. Natl. Acad. Sci. USA, 69, 2110 (1972) or in Gene, 17 107 (1982).

Bacteria of the genus *Bacillus* can be transformed according to the method described, for example, in Molecular & General Genetics, 168, 111 (1979).

Yeast can be transformed according to the method described, for example, in Methods in Enzymology, 194, 182-187 (1991) or in Proc. Natl. Acad. Sci. USA, 75, 1929 (1978)

Insect cells and insects can be transformed according to the method described, for example, in Bio/Technology, 6, 47-55 (1988)

Animal cells can be transformed according to the method described, for example, in Saibo Kogaku (Cell Engineering) extra issue 8, Shin Saibo Kogaku Jikken Protocol (New Cell Engineering Experimental Protocol), 263-267, Shujunsha (1995) or in Virology, 52, 456 (1973).

Thus, a transformant transformed with the expression vector comprising the DNA encoding the polypeptide of the present invention can be obtained.

In cultivating the transformant having bacteria of the genus *Escherichia* or bacteria of the genus *Bacillus* as the host, the appropriate medium used for cultivation is a liquid medium wherein carbon sources, nitrogen sources, inorganic substances and such required for the growth of the said transformant are contained. Carbon sources include glucose, dextrin, soluble starch, sucrose and the like, nitrogen sources include inorganic or organic matter such as ammonium salts, nitrate salts, corn steep liquor, peptone, casein, meat extract, soybean cake, potato extract and the like, and inorganic substances include calcium chloride, sodium dihydrogenphosphate, magnesium chloride and the like. In addition, yeast extract, vitamins, growth promoting factors and such can be added. The pH of the medium is preferably about 5 to 8.

The preferred medium for cultivating bacteria of the genus *Escherichia* is M9 medium comprising glucose and Casamino acids (Miller, Journal of Experiments in Molecular Genetics, 431-433, Cold Spring Harbor Laboratory, New York (1972)) or the like. When necessary, chemicals such as 3β-indolylacrylic acids can be added therein to make the promoter function efficiently.

When using bacteria of the genus *Escherichia* as the host, cultivation is generally carried out at about 15 to 43° C. for about 3 to 24 hours, and aeration or agitation can be conducted when necessary.

When using bacteria of the genus *Bacillus* as the host, cultivation is generally carried out at about 30 to 40° C. for about 6 to 24 hours, and aeration or agitation can be conducted when necessary.

When cultivating a transformant with yeast as the host, the medium to be used is, for example, Burkholder's minimal medium (Bostian, K. L. et al., Proc. Natl. Acad. Sci. USA, 77, 4505 (1980)), or SD medium comprising 0.5% Casamino acids (Bitter, G A. et al., Proc. Natl. Acad. Sci. USA, 81, 5330 (1984)). Preferably, pH of the medium is adjusted to about 5 to 8. Cultivation is generally carried out at about 20 to 35° C. for about 24 to 72 hours, and aeration or agitation is conducted when necessary.

When cultivating a transformant with insect cells or insects as the host, the medium to be used is, for example, Grace's Insect Medium (Grace, T. C. C., Nature, 195,788 (1962)) to which is added appropriate amounts of additives such as immobilized 10% calf serum. Preferably, pH of the medium is adjusted to about 6.2 to 6.4. Cultivation is generally carried out at about 27° C. for about 3 to 5 days, and aeration or agitation is conducted when necessary.

When cultivating a transformant with animal cells as the host, the medium to be used is, for example, MEM medium comprising about 5 to 20% of fetal calf serum (Science, 122, 501 (1952)), DMEM medium (Virology, 8, 396 (1959)), RPMI 1640 medium (Journal of the American Medical Association, 199, 519 (1967)), or 199 medium (Proceeding of the Society for the Biological Medicine, 73, 1 (1950)) Preferably, pH should be about 6 to 8. Cultivation is carried out at about 30 to 40° C. for about 15 to 60 hours, and aeration or agitation is conducted when necessary.

In the foregoing manner, the polypeptide of the present invention can be produced in the transformant intracellularly, in cell membranes, or extracellularly.

The polypeptide of the present invention can be separated and purified from the above culture medium using the methods described below.

When extracting the polypeptide of the present invention from the cultured bacteria or cells, appropriate methods are used in which following cultivation, bacteria or cells are collected by publicly known methods and suspended in an appropriate buffer, the bacteria or cells are then disrupted by ultrasound, lysozyme and/or freeze-thawing, after which the crude extract of the polypeptide is obtained through centrifugation or filtration. The buffer may contain a protein modifier such as urea or guanidine hydrochloride, or a surfactant such as Triton X-100™. Where the polypeptide is secreted into the culture broth, following the completion of cultivation, the bacteria or cells are separated from the supernatant using a publicly known method, and the supernatant is collected.

The polypeptide contained in the cultured supernatant or the extract thus obtained can be purified by appropriately combining publicly known separation and purification methods. Such publicly known separation and purification methods include methods that make use of solubility such as salting out and solvent precipitation, methods that make use of difference in molecular weight such as dialysis, ultrafiltration, gel filtration and SDS-polyacrylamide gel electrophoresis, methods that make use of difference in electric charge such as ion exchange chromatography; methods that make use of the difference in specific affinity such as affinity chromatography, methods that make use of difference in hydrophobicity such as reverse phase high performance liquid chromatography, and methods that make use of difference in isoelectric point such as isoelectrofusing electrophoresis.

Where the polypeptide thus obtained is in a free form, publicly known methods or similar methods can be used to convert it into a salt form, and on the other hand, where it is obtained in a salt form, publicly known methods or similar methods can be used to convert it into a free form or into another salt form.

Further, the polypeptide produced by the recombinant can be optionally modified and parts of the polypeptide can be removed by activating an appropriate protein modifying enzyme before or after purification. Examples of the protein-modifying enzyme include trypsin, chymotrypsin, arginyl endopeptidase, protein kinase and glycosidase.

The activity of the polypeptide of the present invention or salts thereof thus generated can be measured by a binding experiment to a labeled ligand, an enzyme immunoassay using a specific antibody, or such.

Mechano-Sensitive Channel Inhibitors

A mechano-sensitive channel inhibitor contains, for example, one or more of either the polypeptides of the present invention or salts thereof (hereinafter may be described as polypeptides of the present invention). The polypeptides of the present invention can be utilized as mechano-sensitive channel inhibitors. The polypeptides of the present invention are easy to handle, and as shown in the embodiments below, display high inhibiting activity.

Remedies for Atrial Fibrillation

A remedy for atrial fibrillation contains, for example, one or more of either the polypeptides of the present invention or salts thereof. In other words, the present invention can provide pharmaceuticals and pharmaceutical compositions as well. Pharmaceutical compositions are, for example, those that contain the polypeptide of the present invention or salts thereof and a pharmaceutically acceptable carrier.

The remedy for atrial fibrillation comprising the polypeptide of the present invention can be administered parenterally, for example, into the blood vessel of the heart in the form of an injection, or can be used orally, for example, in the form of tablets or capsules. Formulations for injection can be provided in ampules comprising a unit dosage or in containers comprising multiple dosages. Moreover, the preparations can be administered not only to humans but also to other warm-blooded animals. The formulations can be prepared using publicly known preparation methods.

The various preparations can be manufactured using conventional methods by appropriately selecting generally used formulations such as an excipient, a swelling agent, a binder, a moistening agent, a disrupting agent, a lubricant, a surface-active agent, a dispersing agent, a buffer, a preservative, a solubilizing agent, an antiseptic, a sweetening and flavoring agent, a soothing agent, a stabilizing agent, and an isotonic agent. The various agents described above may also contain pharmaceutically acceptable carriers or additives. Such carriers or additives include water, pharmaceutically acceptable organic solvents, collagen, polyvinyl alcohol, polyvinyl pyrrolidone, carboxyvinylpolymer, alginic acid sodium, water-soluble dextran, carboxymethyl starch sodium, pectin, Xanthan gum, gum arabic, casein, gelatin, agar, glycerin, propylene glycol, polyethylene glycol, Vaseline, paraffin, stearate alcohol, stearic acid, human serum albumin, mannitol, sorbitol, and lactose. The additives to be used are selected appropriately or in combination from those described above according to the formulations of the present invention.

The polypeptide of the present invention consisting of the activated component in the forms described above is contained therein, for example, 0.01 to 100% by weight, preferably 0.1 to 90% by weight, more preferably 1 to 50% by weight.

Concerning the dosage of the polypeptide of the present invention, when administered parenterally, the amount of one dosage differs depending on the subject of administration, symptoms and route of administration; and so, if administered in the form of injection to a patient (weighing 60 kg) with atrial fibrillation, for example, the daily dosage is generally about 0.01 to 30 mg, preferably about 0.1 to 20 mg, more preferably about 0.1 to 10 mg. When administered orally to an atrial fibrillation patient (weighing 60 kg), for example, the daily dosage is about 0.1 to 100 mg, preferably about 1.0 to 50 mg, more preferably about 1.0 to 20 mg. The remedy for atrial fibrillation of the present invention is preferably administered once to several times a day for a duration of more than one day.

Identification of the Pharmacophore

In designing the polypeptide of the present invention, the region of the peptide from spider venom (GsMTx-4) consisting of the pharmacophore that is the minimal unit necessary for activation has been estimated with good precision based on a three-dimensional structure.

The pharmacophore can be identified for example in the manner described hereinafter. First, a precise structure estimation of the peptide from spider venom is conducted according to the homology modeling method using a similar peptide with a known three-dimensional structure as the template. Based on the structure thus obtained, a function analysis of the peptide with a modified activated part is performed and the target part for pharmaceutical design is narrowed down. A design that mimics the disulfide bond region of GsMTx-4 is created, and the peptide with a stable structure is designed. GsMTx-4 is known to have a three-dimensional structure of relatively low flexibility that comprises three disulfide bonds, and so the pharmacophore needed for activation is identified by designing several cyclic peptides comprising polar amino acid residues generally often involved in the binding process.

Measurement of the Activity

The activity evaluation method of the peptide of the present invention can be carried out using the publicly known activity evaluation method, preferably using the single channel current recording method employing the patch clamp method described in embodiment 1.

EMBODIMENT 1

Example 1

Search for a Similar Peptide With a Known Structure Showing High Homology to the Sequence of the Peptide From the Spider Venom (GsMTx-4)

A structure with high homology to the amino acid sequence of GsMTx-4 represented by SEQ ID NO:4 was searched among the spider venoms from PDB (Protein Data Bank). Consequently, 10 candidates with high homology to GsMTx-4 were found. The results of the multiple alignment of those candidates are shown in FIG. 1 below.

Of the sequences shown in FIG. 1, 1QK6 (Huwentoxin-I: SEQ ID NO:12) comprising the same cysteine residues, and moreover having almost the same length between the cysteine residues with no insertion or deletion (GsMTx-4 is one residue longer) was selected as the template to narrow down the pharmacophore using the homology modeling method.

Example 2

Estimation of the Three Dimensional Structure of the Peptide of Spider Venom (GsMTx-4)

Figure 4:
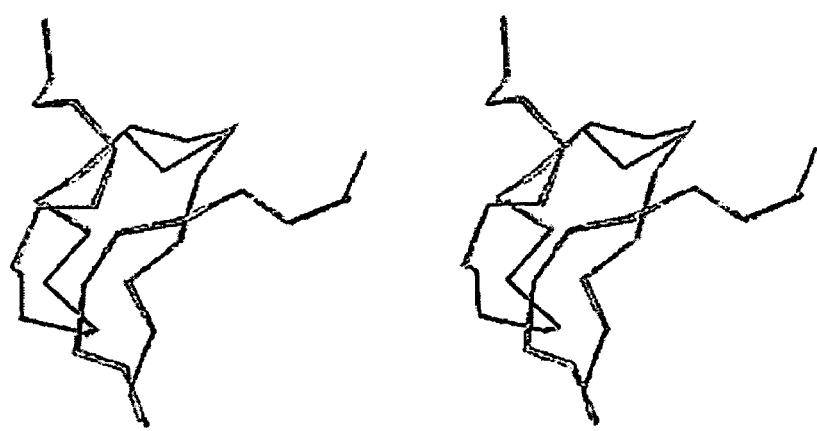
FIG. 4 is a Cα trace of the model of the superimposed Huwentoxin-I and GsMTx-4.

Homology modeling was carried out using the template peptide 1QK6. First, alignment of 1QK6 and GsMTx-4 was performed. The result is shown in FIG. 2. Next, the model structure was constructed with program MODELLER. The superimposition of the constructed structure model of GsMTx-4 and Huwentoxin-I used as the template is shown in FIG. 3 and in FIG. 4. FIG. 3 is a stereo view of the superimposed Huwentoxin-I and GsMTx-4. FIG. 4 is a Cα trace of the model of the superimposed Huwentoxin-I and GsMTx-4. In FIG. 4, the thin lines indicate the template, and the thick lines indicate GxMTx-4.

Figure 5:
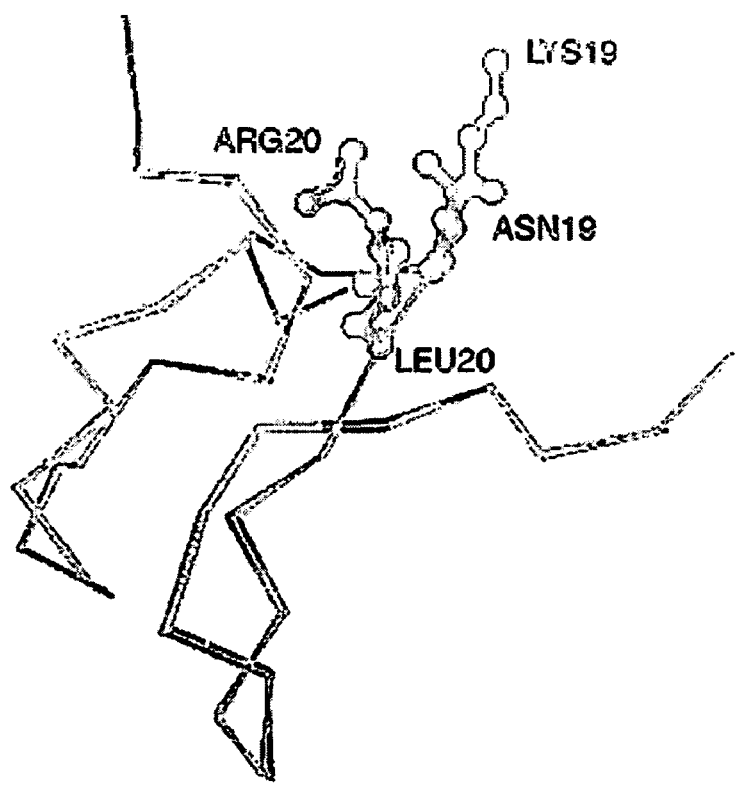
FIG. 5 is a representation of the vicinity of Arg20 considered to be the activity center of Huwentoxin-I.
Figure 6:
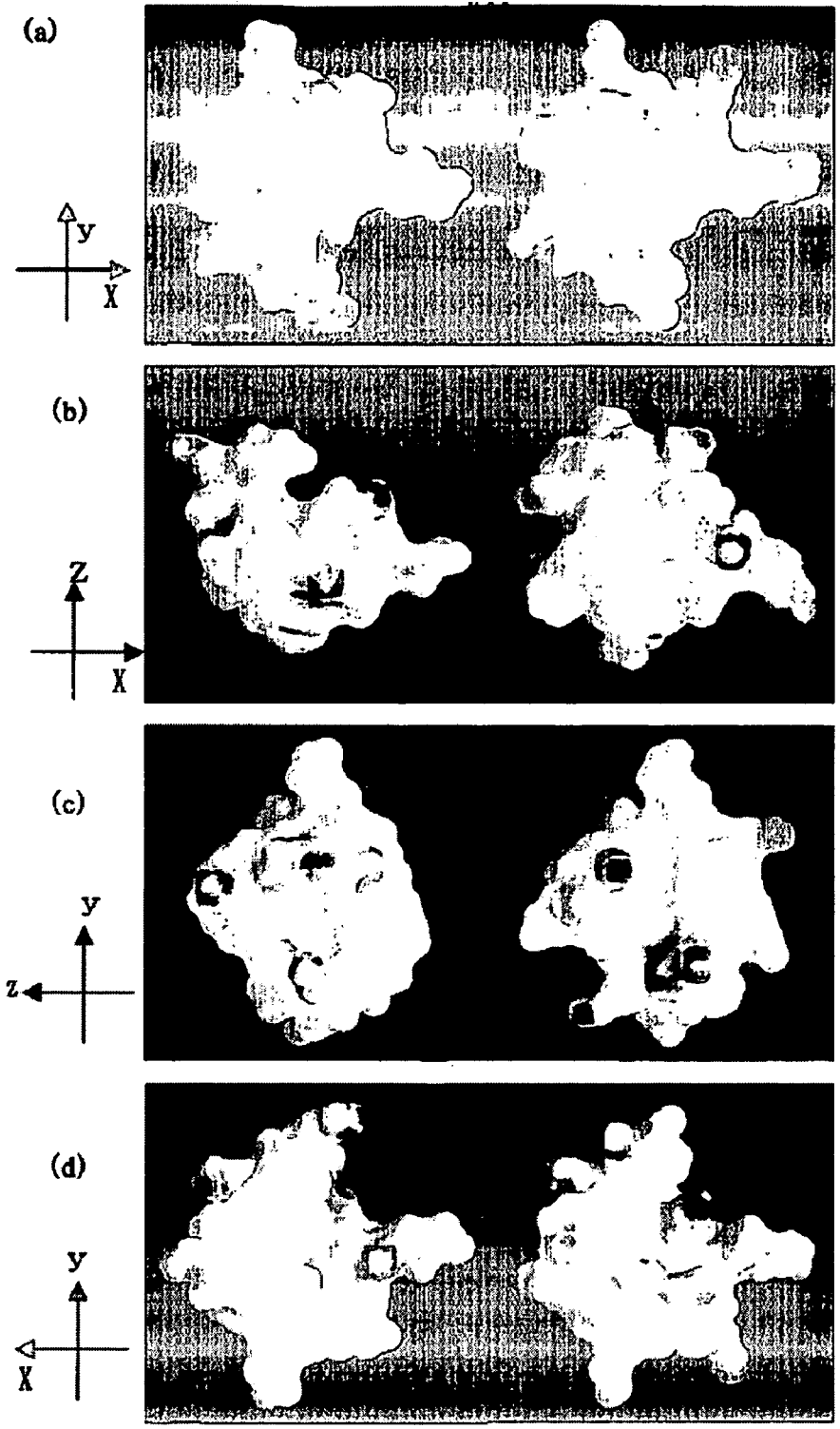
FIGS. 6(a) to 6(d) are representations of the surface structure of a model with Huwentoxin-I (PDB code: 1QK6) as the template.

The vicinity of Arg20 considered to be the activity center of Huwentoxin-I is shown in FIG. 5. In FIG. 5, the thin lines indicate Huwentoxin-I, and the thick lines indicate GsMTx-4. Furthermore, comparisons of the surface structures of Huwentoxin-I and GsMTx-4 are shown in FIG. 6. In FIGS. 6(a) to 6(d), the left side shows Huwentoxin-I, and the right side shows GsMTx-4. FIG. 6(a) is a view from a hydrophobic patch (approximately the same direction as the drawings above). FIG. 6(b) is a view rotated +90° around the x-axis. FIG. 6(c) is a view rotated +90° around the y-axis. FIG. 6(d) is a view rotated 180° around the y-axis. FIG. 6(b) shows that the molecules of the two peptides have quite different forms. The distributions of the residues with isolable side chains also differ, and can be assumed to be concerned with the determination of specificity.

Further, by comparing the structure of GsMTx-4 obtained in a solution using NMR disclosed in Robert et. al., J. Biol. Chem. Vol. 37, pp 3443-3445, 2002 (non-patent document 3 mentioned above) and the structure of GsMTx-4 obtained in the present embodiment, the modeling structure constructed in the present invention can be judged as reflecting the actual structure of GsMTx-4.

Example 3

Design of the Active Peptide and Identification of the Pharmacophore Thereof

Figure 7:
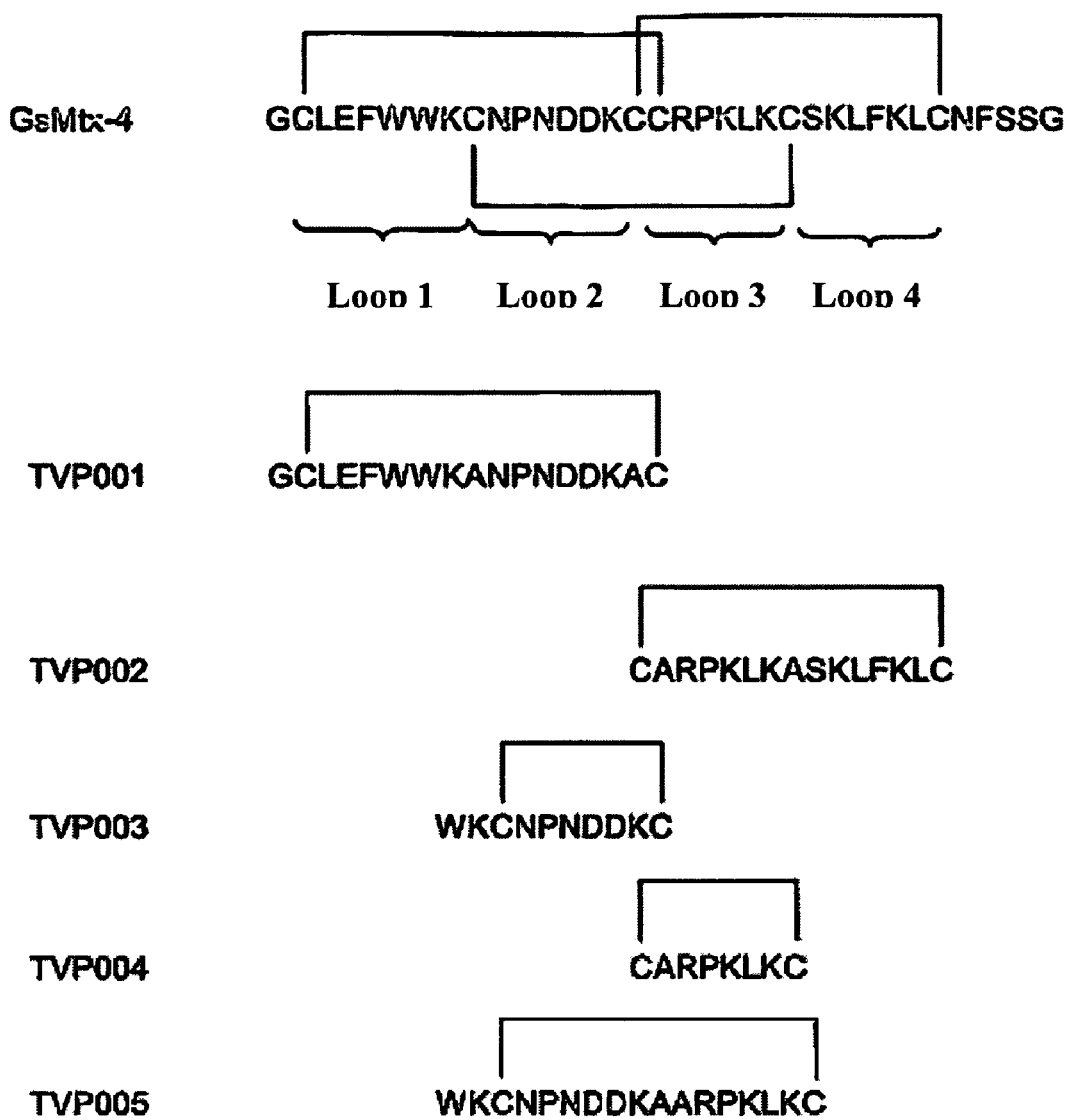
FIG. 7 is a representation of the structure of GsMTx-4 and the structures of the designed peptides.

Based on the modeling structure of GsMTx-4 described above, the policy for designing the peptide fragments was decided. The structure of GsMTx-4 and the designed structure of the peptides are shown in FIG. 7. GsMTx-4 comprises four loops formed by three disulfide bonds as indicated in the sequence structure formula shown in FIG. 7. Therefore, five peptides TVP001 to TVP005 were designed to determine the loop contributing to the inhibiting activity. In these peptides, cysteines at the regions not composing the loops have been substituted with alanines. TVP001 (SEQ ID NO:14) comprises loops 1 and 2, TVP002 (SEQ ID NO:15) comprises loops 3 and 4, TVP003 (SEQ ID NO:1) comprises loop 2, TVP004 (SEQ ID NO:2) comprises loop 3, and TVP005 (SEQ ID NO:3) comprises loops 2 and 3.

Bioassay of the Designed Peptides

Activity assay of the peptides was carried out by the most reliable single channel current recording method using the patch clamp method. As the subject of the assay, $Ca^{2+}$ dependant BigK channel (Kawakubo et. Am J Physiol, 276: H1827.1999) derived from heart muscle was employed. By applying this channel to the expressed ventricle muscle of chicken or to CHO cells force-expressing the cDNA of this channel with the cell-attached patch clamp method, an inside-out excised patch was formed, and single channel current recordings were taken under a fixed membrane potential. Assuming that the designed synthetic peptide blocks the channel extracellularly the same as GsMTx-4, the space a fixed distance above the glass pipette used for recording was filled with the peptide of a known concentration beforehand, and administration was carried out by back-fill which utilizes diffusion to reach the channel, With this method, the concentration of the peptide inside the pipette reaches equilibrium 15 to 20 minutes after the start of diffusion, and so the dissociation constant of the peptide can be estimated from the inhibition ratio at 20 minutes and onwards. Or, the relative inhibition of the peptide can be estimated from the time taken for inhibition. If the exact dissociation constant of the peptide is to be calculated, it is necessary to prepare an outside-out excised patch, take single channel current recordings, analyze the inhibition effects of various peptides with different concentration, and obtain a dose-inhibition curve; however, as this method requires special technology and as this is the primary screening of the various designed synthetic peptides, the assay method combining the inside-out excised patch and back-fill described above was used to make a rough estimate of the inhibition effects of the peptides. Taking into consideration the results obtained for GsMTx-4, the concentration of the peptide was maintained at 10pM. Concerning the scale of evaluation, the channel's open probability (Po, indicated in percentage) was used, and the level of inhibition was expressed by the inhibition ratio (percentage) with the control (prior to the administration of the peptide) as the standard, or by the time taken for inhibition.

Results of the Assay

Of the five designed synthetic peptides, TVP003, TVP004 and TVP005 displayed inhibiting activity. Therefore, mutation TVP017 (SEQ ID NO:16) in which the $3^{rd}$ R from the N-terminus of TVP004 had been substituted by A and mutation TVP019 in which the $7^{th}$ K from the N-terminus of TVP004 had been substituted by A were synthesized, and the inhibiting activity was measured using the bioassay described above; as a result, these synthetic peptides were also found to show inhibiting activity.

Figure 8:
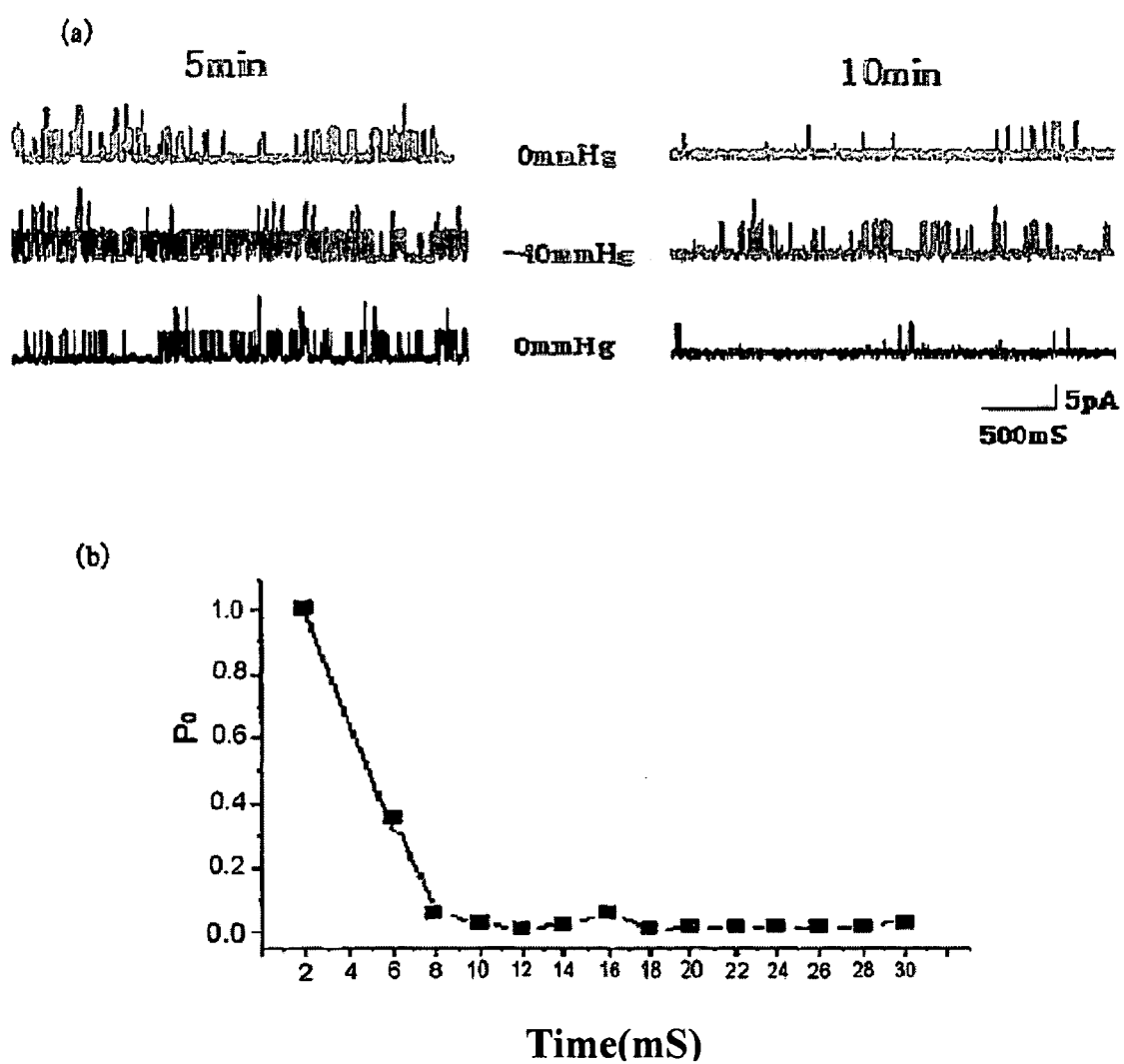
FIGS. 8(a) and 8(b) are representations of the inhibiting activity of TVP003.

The inhibiting activity of TVP003 is shown in FIG. 8. FIG. 8(a) is a representation of single channel current recordings. FIG. 8(b) represents the channel's open probability (Po). As indicated in FIG. 8, TVP003 showed 100% inhibition after 8 minutes, and so the dissociation constant of TVP003 was estimated as μM order or lower. It is suggested from this value that TVP003 shows inhibiting activity of a level the same as or higher than the natural peptide from spider venom, GsMTx-4.

The inhibiting activity of TVP004 is shown in FIG. 9. FIG. 9(a) is a representation of the single channel recordings. FIG. 9(b) represents the channel's open probability (Po) As indicated in FIG. 9, at 10 μM, TVP004 showed inhibition activity of about 60% after 8 minutes, and 95% after 16 minutes, displaying a relatively high level of inhibition activity.

The inhibition activity of TVP005 is shown in FIG. 10. FIG. 10(a) is a representation of the single channel recordings. FIG. 10(b) represents the channel's open probability (Po). As indicated in FIG. 10, TVP005 showed about 60% inhibition after 20 minutes, and so the dissociation constant thereof was estimated as approximately about The inhibition activity of TVP017 is shown in FIG, 11. FIG. 11(a) is a representation of the single channel recordings. FIG. 11(b) represents the channel's open probability (Po). As indicated in FIG. 11, TVP017 showed 100% inhibition after 6 minutes, and so was found to display an even higher level of inhibition than TVP003. It is suggested from this value that TVP017 shows inhibition activity of a higher level than the natural peptide from spider venom, GsMTx-4.

Figure 12:
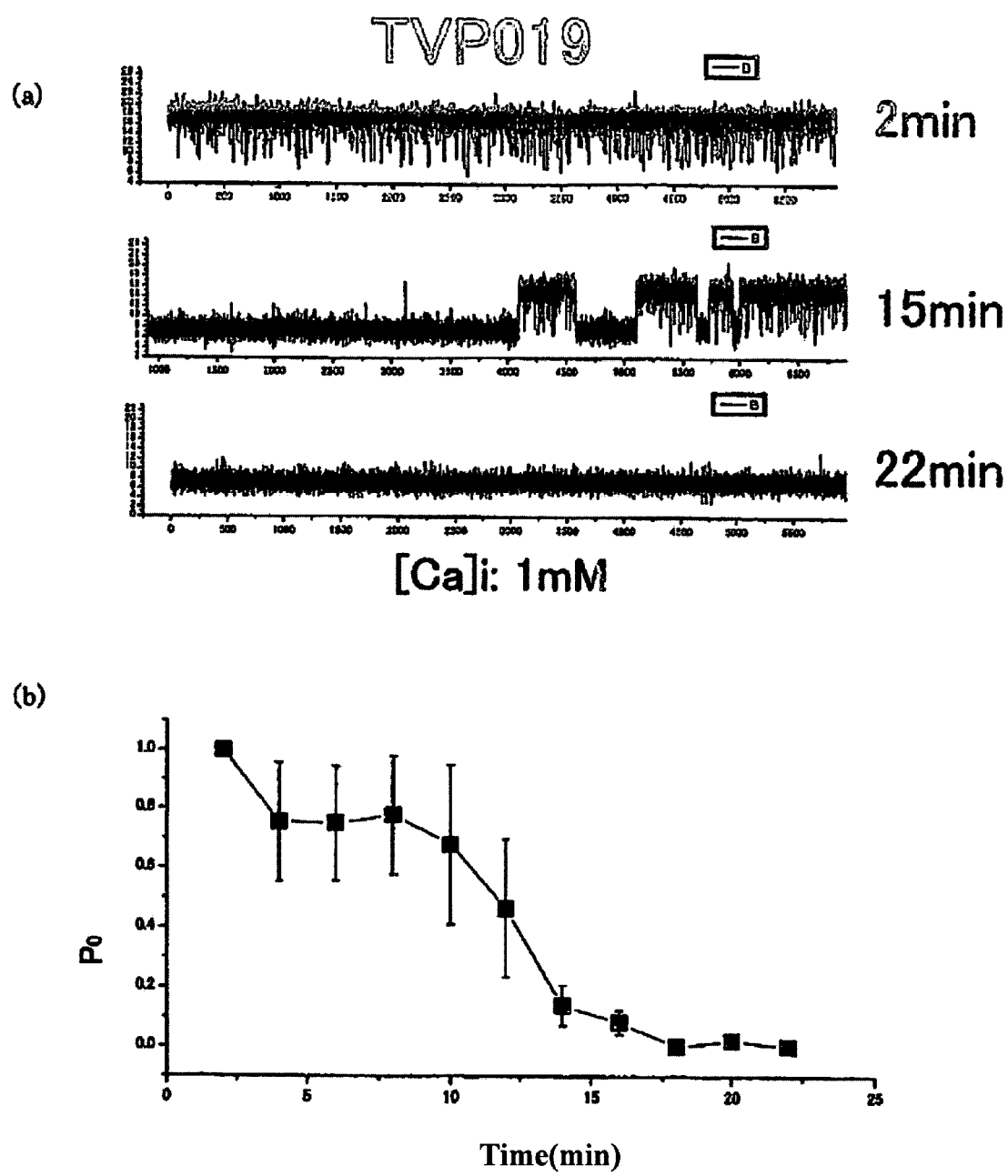
FIGS. 12(a) and 12(b) are representations of the inhibition activity of TVP019.

The inhibition activity of TVP019 is shown in FIG. 12. FIG. 12(a) is a representation of the single channel recordings. FIG. 12(b) represents the channel's open probability (Po). As indicated in FIG. 12, TVP019 showed approximately 80% inhibition after 14 minutes.

EMBODIMENT 2 SPECIFICITY OF THE PEPTIDE TO THE CHANNEL

Example 4

Specificity of the Active Peptide to a Mechano-Sensitve Channel

Figure 13:
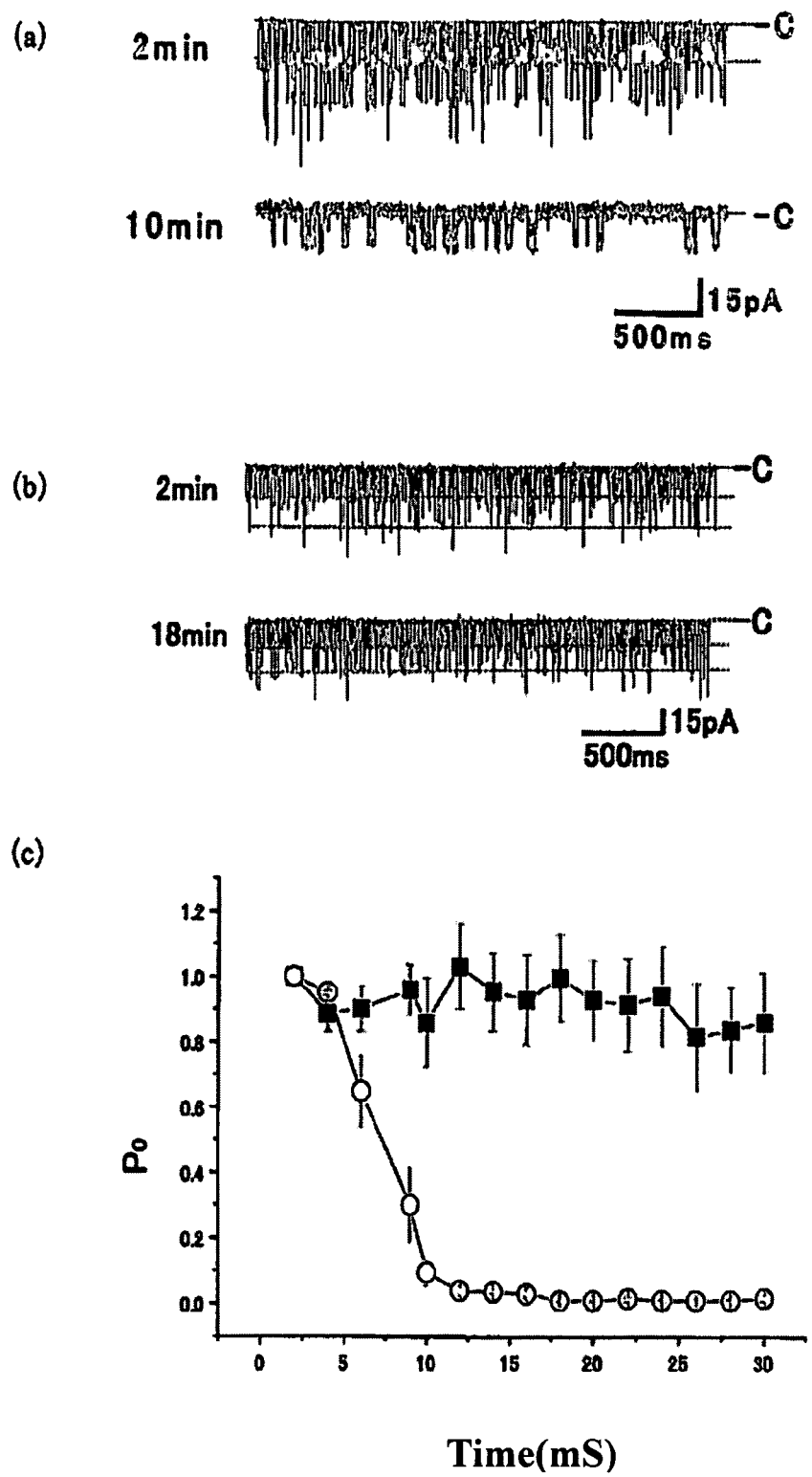
FIGS. 13(a) to 13(c) are results of the study into the specificity of the active peptide to a mechano-sensitive channel.

The specificity of the peptide of the present invention to a mechano-sensitive channel was examined. TVP003 was used as the active peptide, and myocardial SA channel, the same as that utilized in example 3, was used as the channel. This channel has a STREX sequence consisting of 59 amino acids at the C-terminus, and the STREX-deletion-mutant deleted of that sequence loses almost all extension activity, thus becoming a common Ca dependant bigK channel (SAKCA: Tang, Naruse, Sokabe, J Membr Biol, 169:185-200, 2003). FIG. 13 is the result of study into the specificity of the active peptide to a mechano-sensitive channel. FIG. 13(a) is a representation of the single channel recordings related to the myocardial SA channel of TVP003. FIG. 13(b) is a representation of the single channel recordings related to the STREX-deletion-mutant of TVP003. FIG. 13(c) represents the channel's open probability (Po). It can be seen from FIG. 13 that GsMTx-4 and TVP003 inhibit the wild-type SA channel but do not inhibit the STREX-deletion-mutant hardly at all. Therefore, GsMTx-4 and TVP003 can be considered as specifically acting only on a channel with extension activity.

INDUSTRIAL APPLICABILITY

According to the present invention, it is possible to obtain a novel polypeptide that specifically inhibits the activity of a mechano-sensitive channel.

Utilizing a polynucleotide encoding such a polypeptide of the present invention, a recombinant vector comprising this polynucleotide, and a transformant transformed by the recombinant vector, the polypeptide of the present invention can be produced in large quantities.

A mechano-sensitive channel inhibitor comprising the polypeptide of the present invention or salts of the polypeptide of the present invention is useful for manufacturing a reagent related to a mechano-sensitive channel.

A remedy for atrial fibrillation comprising the polypeptide of the present invention or salts of the polypeptide of the present invention can efficiently treat atrial fibrillation.

The invention claimed is:

1. A purified polypeptide or salt thereof consisting of: SEQ ID NO:1, and having a disulfide bond between two of the cysteines contained in SEQ ID NO:1.

2. A medicament for atrial fibrillation comprising the polypeptide or salt thereof described in claim 1.

* * * * *